United States Patent [19]

Boger

[11] Patent Number: 4,665,052
[45] Date of Patent: * May 12, 1987

[54] RENIN INHIBITORS CONTAINING HOMOPHE[8] AND A C-TERMINAL AMIDE CYCLE

[75] Inventor: Joshua S. Boger, Bryn Mawr, Pa.

[73] Assignee: Merck & Co., Inc., Rahway, N.J.

[*] Notice: The portion of the term of this patent subsequent to Nov. 27, 2001 has been disclaimed.

[21] Appl. No.: 593,755

[22] Filed: Mar. 27, 1984

[51] Int. Cl.[4] .................. A61K 37/43; C07K 5/12; C07K 5/10; C07K 5/08; C07K 7/06
[52] U.S. Cl. .................................... 514/11; 530/317; 514/16; 514/17; 514/18
[58] Field of Search .................. 260/112.5 R; 514/11, 514/16, 17, 18; 530/317

[56] References Cited

U.S. PATENT DOCUMENTS

| | | | |
|---|---|---|---|
| 3,784,686 | 2/1974 | Miller | 260/112.5 R |
| 3,873,681 | 3/1975 | Miller | 260/112.5 R |
| 4,384,994 | 5/1983 | Veber et al. | 260/112.5 R |
| 4,397,786 | 8/1983 | Evans et al. | 260/112.5 R |
| 4,485,099 | 11/1984 | Boger et al. | 260/112.5 R |

FOREIGN PATENT DOCUMENTS

0077028  4/1983  European Pat. Off.
0077029  4/1983  European Pat. Off.

OTHER PUBLICATIONS

Umezawa et al., J. Antibiot. (Tokyo), 23:259–262, 1970.
Gross et al., Science, 175:656, 1971.
Tewsbury et al., Circulation, 59, 60, Supp. II:132, 10/79.
Poulsen et al., Biochem. Biophys. Acta, 452:533–537, 1976.
Skeggs, Jr. et al., J. Exp. Med., 106:439–453, 1957.
Kokubu et al., Biochem. Pharmacol., 22:3217–3223, 1973.
Burton et al., Biochemistry, 14:3892–2898, 1975.
Poulsen et al., Biochemistry, 12:3877–3882, 1973.
Haber and Burton, Fed. Proc. Fed. Am. Soc. Exp. Biol., 38:2768–2773, 1979.
Hallett, Szelke, and Jones, Nature, 299, 555, 1982.
Hallett, Szelke, and Jones, Hypertension, 4, Supp. 2, 59, 1982.
Powers et al., Acid Proteases, Structure, Function and Biology, Plenum Press, 1977, 141–157.
Tang et al., Trends in Biochem. Sci., 1:205–208, 1976.
Tang et al., J. Biol. Chem., 251:7088–94, 1976.
Borger et al., Nature, 303:81–84, 1983.
Marshall, Federation Proc., 35:2494–2501, 1976.
Burton et al., Proc. Natl. Acad. Sci. USA, 77:5476–5479, 9/80.
Suketa et al., Biochemistry, 14:3188, 1975.
Swales, Pharmac. Ther., 7:173–201, 1979.
Kokubu et al., Nature, 217:456–457, 2/3/68.
Matsushita et al., J. Antibiotics, 28:1016–1018, 12/75.
Lazar et al., Biochem. Pharma., 23:2776–2778, 1974.
Miller et al., Biochem. Pharma., 21:2941–2944, 1972.
Haber, Clinical Science, 59:7s–19s, 1980.
Rich et al., J. Org. Chem., 43:3624, 1978.
Rich et al., J. Med. Chem., 23:27, 1980.
S. Takagi and K. Hayashi, Chem. Pharm. Bull. 7, 183, 1959.

*Primary Examiner*—Delbert R. Phillips
*Attorney, Agent, or Firm*—Richard A. Elder; Raymond M. Speer; Hesna J. Pfeiffer

[57] ABSTRACT

Renin inhibitory peptides of the formula $$A-B-B-D-E-N(H)-C(H)(CH_2-CH(OH)-(CH_2)_n-N(H)-)-C(=O)-N(H)-C(H)(R^4)-C(=O)-N(H)-C(H)((CH_2)_m-R^3)-C(=O)-N(H)-C(H)(R^5)-C(=O)-F \quad (I.)$$

and analogs thereof inhibit renin and are useful for treating various forms of renin-associated hypertension and hyperaldosteronism.

4 Claims, No Drawings

RENIN INHIBITORS CONTAINING HOMOPHE[8] AND A C-TERMINAL AMIDE CYCLE

BACKGROUND OF THE INVENTION

1. Field of the Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_i$):

| Class | $K_i$ (M) |
| --- | --- |
| Renin antibody | probably $10^{-6}$ |
| Pepstatin | $10^{-6}$–$10^{-7}$ |
| Phospholipids | $10^{-3}$ |
| Substrate analogs | |
| Tetrapeptides | $10^{-3}$ |
| Octa- to tridecapeptides | $10^{-5}$–$10^{-6}$ |

Umezawa et al., in *J. Antibiot.* (Tokyo) 23: 259–262, 1970, reported the isolation of a peptide from actinomyces that was an inhibitor of aspartyl proteases such as pepsin, cathepsin D, and renin. This peptide, known as pepstatin, was found by Gross et al., *Science* 175: 656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

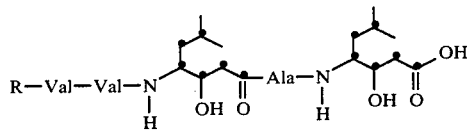

To date, many efforts have been made to prepare a specific renin inhibitor based on substrate analogy. Since the human renin substrate has only recently been elucidated (Tewksbury et al., *Circulation* 59, 60, Supp. II: 132, October 1979), heretofore substrate analogy has been based on the known pig renin substrate. While the human and pig renin substrates are not the same, the substrate analogy based on pig renin has always been considered acceptable in the art as predictive of human renin inhibitory activity because of the closely related activity of the two renins. Thus, while pig renin does not cleave the human renin substrate, human renin, on the other hand, does cleave the pig renin substrate. See Poulsen et al., *Biochim. Biophys. Acta* 452: 533–537, 1976; and Skeggs, Jr. et al., *J. Exp. Med.* 106: 439–453, 1957. Moreover, the human renin inhibitory activity of the peptides of the present invention most active in inhibiting pig renin has been confirmed, thus providing further evidence of this accepted correlation between human and pig renin activity.

It has been found, for example, using pig renin substrate analogy, that the octapeptide sequence extending from histidine-6 through tyrosine-13 has kinetic parameters essentially the same as those of the full tetradecapeptide renin substrate. The amino acid sequence of the octapeptide in pig renin substrate is as follows:

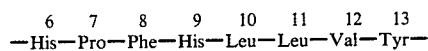

Renin cleaves this substrate between $Leu^{10}$ and $Leu^{11}$.

Kokubu et al., *Biochem. Pharmacol.* 22: 3217–3223, 1973, synthesized a number of analogs of the tetrapeptide found between residues 10 to 13, but while inhibition could be shown, inhibitory constants were only of the order of $10^{-3}$M.

Analogs of a larger segment of renin substrate were also synthesized: Burton et al., *Biochemistry* 14: 3892–3898, 1975, and Poulsen et al., *Biochemistry* 12: 3877–3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, *Fed. Proc. Fed. Am. Soc. Exp. Biol.* 38: 2768–2773, 1979.

More recently, Hallett, Szelke, and Jones, in work described in European Patent Publication No. 45,665 *Nature*, 299, 555 (1982), and *Hypertension*, 4, Supp. 2, 59 (1981), have replaced the Leu-Leu site of renin cleavage by isosteric substitution, and obtained compounds with excellent potency.

Powers et al., in *Acid Proteases, Structure, Function and Biology*, Plenum Press, 1977, 141-157 have suggested that in pepstatin, statine occupies the space of the two amino acids on either side of the cleavage site of a pepsin substrate, and Tang et al., in *Trends in Biochem. Sci.*, 1: 205-208 (196) and *J. Biol. Chem.*, 251: 7088-94, 1976, have proposed that the statine residue of pepstatin resembles the transition state for pepsin hydrolysis of peptide bonds. However, the applicability of these concepts to renin inhibitors is not taught in any of these references, and would be speculative due to the known high degree of specificity of the renin enzyme.

Veber and Rich, in U.S. Pat. No. 4,384,994 and published European Patent Application No. 0,077,029; Evans and Rittle, in U.S. Pat. No. 4,397,786; Veber and Boger, in published European Patent Application No. 0,077,028; Boger et al, *Nature*, 303: 81-84 (1983); have all described renin inhibitory peptides containing statine. However, none of these references describe or suggest the HomoPhe[8] improvement of the present invention and the significant increase in renin inhibitory activity obtainable therewith.

For other articles describing previous efforts to devise renin inhibitors, see Marshall, *Federation Proc.* 35: 2494-2501, 1976; Burton et al., *Proc. Natl. Acad. Sci. USA* 77: 5476-5479, September 1980; Suketa et al., *Biohemistry* 14: 3188, 1975; Swales, *Pharmac. Ther.* 7: 173-201, 1979; Kokubu et al., *Nature* 217: 456-457, February 3, 1968; Matsushita et al., *J. Antibiotics* 28: 1016-1018, December 1975; Lazar et al., *Biochem. Pharma.* 23: 2776-2778, 1974; Miller et al., *Biohem. Pharma.* 21: 2941-2944, 1972; Haber, *Clinical Science* 59: 7s-19s, 1980; and Rich et al., *J. Org. Chem.* 43: 3624, 1978, and *J. Med. Chem.* 23: 27, 1980.

DETAILED DESCRIPTION OF THE INVENTION AND PREFERRED EMBODIMENTS

In accordance with the present invention there are provided renin inhibitory peptides of the formula:

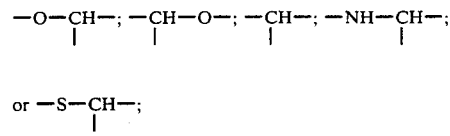
(I.)

wherein:

A is hydrogen; or

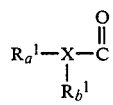

where X is —O—;

—O—CH—; —CH—O—; —CH—; —NH—CH—;

or —S—CH—;

and $R_a^1$ and $R_b^1$ may be the same or different and are hydrogen; Y—(CH$_2$)$_p$— or —(CH$_2$)$_{p'}$—CH=CH—(CH$_2$)$_{p''}$, where Y is C$_{1-4}$alkyl; hydrogen; aryl; C$_{3-7}$cycloalkyl; or C$_{3-7}$cycloalkyl or aryl substituted with up to five members independently selected from the group consisting of C$_{1-8}$alkyl, trifluoromethyl, hydroxy, C$_{1-4}$alkoxy, and halo;

p is 0 to 5; and p' and p" are independently 0 to 2; except that where X is —O—, only one of $R_a^1$ or $R_b^1$ is present;

B is absent; glycyl; sarcosyl; or

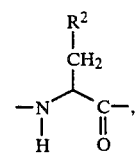

where R$^2$ is hydrogen; C$_{1-4}$ alkyl; hydroxy C$_{1-4}$alkyl; aryl; aryl substituted with up to three members selected from the group consisting of C$_{1-4}$alkyl, trifluoromethyl, hydroxy, C$_{1-4}$alkoxy, and; halo; indolyl; 4-imidazolyl; amino C$_{2-4}$ alkyl; guanidyl C$_{2-3}$ alkyl; or methylthiomethyl;

D is absent; or

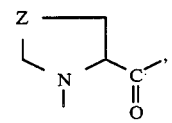

where Z is —(CH$_2$)$_1$— and 1 is 1 or 2; or —S—;

E is

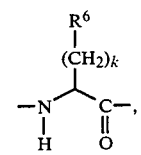

where k is 2 to 4; and R$^6$ is hydrogen; C$_{1-4}$alkyl; aryl; substituted with up to three members selected from the group consisting of C$_{1-4}$alkyl, trifluoromethyl, hydroxy, C$_{1-4}$alkoxy, and halo; or indolyl;

F is absent; or glycyl;

R$^3$ is C$_{3-6}$ alkyl; C$_{3-7}$ cycloalkyl; aryl; or C$_{3-7}$cycloalkyl or aryl substituted with up to three members selected from the group consisting of C$_{1-4}$alkyl, trifluoromethyl, hydroxy, C$_{1-4}$alkoxy, and halo;

R$^4$ is hydrogen; or

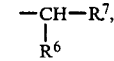

where R⁷ is hydrogen; C₁₋₄alkyl; hydroxy; or C₃₋₇cycloalkyl; and R⁶ is as defined above;
R⁵ is hydrogen;

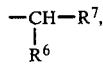

where R⁶ and R⁷ are as defined above; or —(CH₂)_q—R⁸, where q is 0 or 1–4; and R⁸ is heterocyclic; heterocyclic substituted with up to five members independently selected from the group consisting of C₁₋₆alkyl, hydroxy, trifluoromethyl, C₁₋₄alkoxy, halo, aryl, aryl C₁₋₄alkyl, amino, and mono- or di-C₁₋₄alkylamino; guanidyl C₂₋₃alkyl; or amino C₁₋₄alkyl;

m is 1 to 4;

n is 0 to 4; and wherein all of the asymmetric carbon atoms have an S configuration, except fot those in the A, B and D substituents, which may have an S or R configuration; and a pharmaceutically acceptable salt thereof.

While both the S and R chiralities for asymmetric carbon atoms in the A, B and D substituents are included in the peptides of the present invention, preferred chiralities are indicated in the description which follows.

In the above definitions, the term "alkyl" is intended to include both branched and straight chain hydrocarbon groups having the indicated number of carbon atoms.

The term "halo" means fluoro, chloro, bromo and iodo.

The aryl substituent represents phenyl, and naphthyl.

The heterocyclic substituent recited above represents any 5- or 6-membered aromatic ring containing from one to three heteroatoms selected from the group consisting of nitrogen, oxygen, and sulfur; having various degrees of saturation; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substitutents are also preferred. Thus, piperidine is a preferred heterocyclic substituent. Other preferred heterocyclic substituents are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Where the heterocyclic substituent itself is substituted, it is preferred that the substituent be arylC₁₋₄alkyl.

Then novel renin inhibitory peptides of the present invention may also be described in terms of common amino acid components and closely related analogs thereof, in accordance with the following formula:

A-B-B-D-E-G-Sta-H-I-F (II).

The A, B, D, E and F components correspond to the same portions of Formula I.

In formula II, Sta represents the unusual amino acid statine and its closely related analogs, and its presence constitutes a unique feature of the renin inhibitory peptides of the present invention. Statine may be named as 4(S)-amino-3(S)-hydroxy-6-methylheptanoic acid, and may be represented by the following formula:

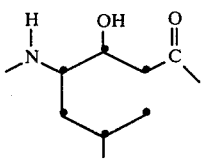

(III)

As shown in Formula III above, the delta-substituent in naturally-occurring statine is isopropyl, or a leucine sidechain, essentially. As shown in Formula I by the R³ substitutents, the isopropyl group may be replaced by higher alkyl groups up to six carbon atoms, cycloalkyl groups containing from three to seven carbon atoms, aryl, and C₃₋₇cycloalkyl or aryl substituted with up to three members selected from the group consisting of C₁₋₄alkyl, trifluoromethyl, hydroxy, C₁₋₄alkoxy, fluoro, chloro, bomo, and iodo. A phenyl substituent and a cyclohexyl substituent are especially preferred. These modifications of the naturally-occurring statine structure are in accordance with the hydrophobicity considered necessary to maintain the inhibitory activity of the total peptide.

The remaining common amino acid components of Formula II are as follows:

A has the same meaning as above in Formula I;

B is Ala, Leu, Ser, Thr, Phe, Tyr, Trp, His, Lys, Orn, Arg, or Met;

D is Pro;

E is HomoPhe, BisHomoPhe, HomoTyr or HomoTrp;

G is one end of the cyclical structure: Lys, Orn, HLys (2S-amino-6-amino-heptanoic acid) or DAB (2S-amino-4-butyric acid);

H is Gly, Ala, Val, Leu, Ile, Ser, Thr, Phe, Tyr, or Trp;

I is the same as H and may also be Lys, Orn, Arg, or His; and

F is Gly and the other end of the cyclical structure, or, when absent, I is that other end.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formula I and its definitions. Thus, the peptides of Formula II and its definitions, including the derivatives of natually-occurring statine represented by the definitions of the R³ substituent in Formula I, represent preferred peptides of the present invention.

Preferred inhibitory peptides of the present invention are the following:

IBU—His—Pro—Hph¹—Lys—Sta—Leu—Phe ⎤
                                      ⎦

IBU²—His—Pro—Hph—Orn—Sta—Leu—Phe ⎤
                                  ⎦

IBU—His—Pro—Hph—DAB¹—Sta—Leu—Phe—Gly ⎤
                                       ⎦

-continued

IBU—His—Pro—Hph—HLys⁴—Sta—Leu—Phe ⌐
                                    ⌐⌐⌐⌐⌐⌐⌐⌐⌐⌐⌐⌐⌐⌐⌐⌐⌐

IBU—His—Pro—Hph—Orn—Sta—Leu—Phe—Gly ⌐

IBU—His—Pro—Hph—Lys—Sta—Leu—Phe—Gly ⌐

BOC⁵—Hph—Lys—Sta—Leu—Phe ⌐

IVA⁶—His—Pro—Hph—Lys—Sta—Leu—Phe ⌐

IVA—His—Pro—Hph—Lys—AHPPA⁷—Leu—Phe ⌐

BOC—Hph—Lys—ACHPA⁸—Ile—His ⌐

IVA—His—D-Pro—Hph—Lys—AHPPA—Leu—Phe ⌐

IVA—His—D-Pro—Hph—Lys—ACHPA—Leu—Phe ⌐

IVA—His—D-Pro—Hph—Lys—ACHPA—Ile—His ⌐

¹Hph = L-Homophenylalanine.
²IBU = Iso-butyryl.
³DAB = 2S—Amino-4-aminobutyric acid.
⁴HLys = Homolysine, 2S—amino-6-aminoheptanoic acid.
⁵BOC = Tert-butyloxycarbonyl.
⁶IVA = Iso-valeryl.
⁷AHPPA = (3S, 4S)-4-Amino-3-hydroxy-5-phenyl-pentanoic acid.
⁸ACHPA = (3S, 4S)-4-Amino-5-cyclohexyl-3-hydroxy-pentanoic acid.

The inhibitory peptides of the present invention may be better appreciated in terms of substrate analogy from the following illustration of Formula I alongside the octapeptide sequence of a portion of the pig renin substrate, which renin cleaves between Leu¹⁰ and Leu¹¹:

Pro Phe His Leu Leu Val Tyr
 7   8   9  10(11) 12  13(14)

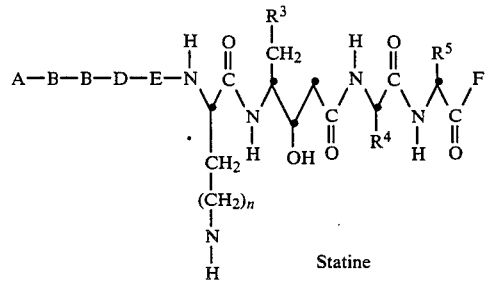

Statine (I.)

As can be seen, a unique aspect and essential feature of the present invention is the substitution of the single statine or derivative amino acid component for the double amino acid sequence: Leu¹⁰-Leu¹¹ in the endogenous pig renin substrate. It is believed that substitution of statine for both leucine amino acids rather than just one leucine results in an improved substrate analogy due to the greater linear extent of statine as compared to a single leucine component. Thus, statine more closely approximates Leu-Leu in linear extent, and thereby provides a better "fit" to the renin enzyme.

The inhibitory peptides of the present invention may also be better appreciated in terms of substrate analogy from the following illustration of Formula I alongside the octapeptide sequence of a portion of the human renin substrate, which renin cleaves between Leu¹⁰ and Val¹¹:

Pro Phe His Leu Val Ile His
 7   8   9  10(11) 12  13(14)

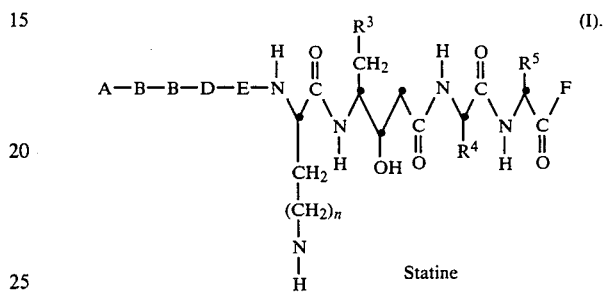

Statine (I).

As can be seen, a unique aspect and essential feature of the present invention is the substitution of the single statine or derivative amino acid component for the double amino acid sequence: Leu¹⁰-Val¹¹ in the endogenous human renin substrate. It is believed that substitution of statine for both the leucine and valine amino acids rather than just the leucine results in an improved substrate analogy due to the greater linear extent of statine as compared to a single leucine component. Thus, statine more closely approximates Leu-Val in linear extent, and thereby provides a better "fit" to the human renin enzyme.

In the endogenous substrate it is also preferred to substitute Leu for Val¹² and Phe for Tyr¹³ in order to enhance the inhibitory activity of the resulting peptide.

The Formula I compounds can be used in the form of alts derived from inorganic or organic acids and bases. Included among such acid addition salts are the following: acetate, adipate, alginate, aspartate, benzoate, benzenesulfonate, bisulfate, butyrate, citrate, camphorate, camphosulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel peptides of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

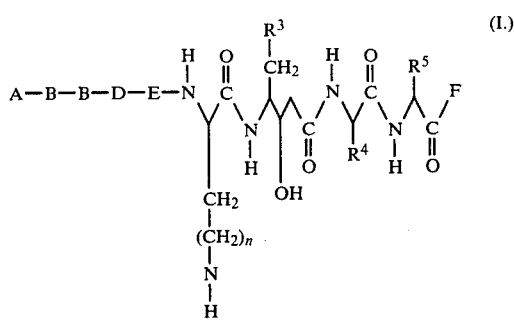

wherein A, B, D, E, $R^3$, $R^4$, $R^5$ and F have the same meaning as recited further above for Formula I; wherein all of the asymmetric carbon atoms have an S configuration, except for those in the A, B and D substituents, which may have an S or R configuration; and a pharmaceutically acceptable salt thereof.

Also, in accordance with the present invention there is still further provided a method of treating renin-associated hypertension and hyperaldosteronism, comprising administering to a patient in need of such treatment, a therapeutically effective amount of a peptide of the formula:

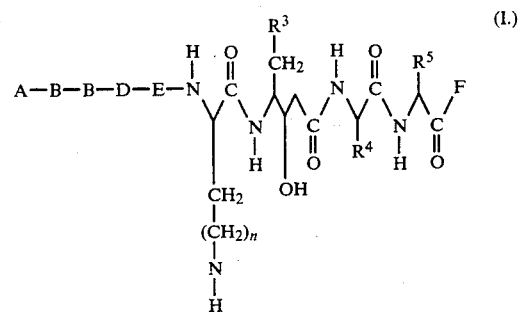

wherein A, B, D, E, $R^3$, $R^4$, $R^5$ and F have the same meaning as recited further above for Formula I; wherein all of the asymmetric carbon atoms have an S configuration, except for those in the A, B and D substituents, which may have an S or R configuration; and a pharmaceutically acceptable salt thereof.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the in vivo method, a novel peptide of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids, which will be described in more detail below. The unusual amino acid, statine, may be prepared in accordance with the procedure described by Rich et. al., *J. Org. Chem.* 43: 3624 (1978).

A general method of preparation may be described in the following terms; wherein amino acids forming peptides of various lengths are sequentially assigned a Roman numeral for each peptide, rather than on the basis of a position in the overall peptide Formula I:

A method of preparing a peptide of formula I, said peptide being comprised of from four to nine amino acids identified as I through IX, amino acid (AA) I being at the C-terminus of said peptide, and amino acid (AA) IV through IX, depending upon the number of amino acids present, being at the N-terminus of said peptide, to which substituent A is attached, said peptide of Formula I being cyclical by virtue of a peptide bond between AA I and AA IV or AA V, comprising the steps of:

(A) treating an ester of the C-terminus amino acid (AA I) with the next adjacent amino acid (AA II) of said peptide, the amino group of said amino acid being protected by a protecting group, in the presence of a condensing agent, whereby a dipeptide of the two amino acids (AA I and II) is formed;

(B) deprotecting the dipeptide formed in Step (A) by removing the protecting group from the amino group of AA II;

(C) treating the dipeptide of AA I and AA II with AA III, the amino group of which is protected by a protecting group, in the presence of a condensing agent, whereby a tripeptide of AA I, AA II and AA III is formed;

(D) deprotecting the tripeptide formed in Step (C) by removing the protecting group from the amino group of AA III;

(E) treating the tripeptide of AA's I-II-III with AA IV, the amino group of which is protected by a protecting group, in the presence of a condensing agent, whereby a quadripeptide of AA's I-II-III-IV is formed;

(F) deprotecting the quadripeptide formed in Step (E) by removing the protecting group from the amino group of AA IV;

(G) forming the methyl ester of AA I if said ester is not employed initially;

(H) cyclizing the quadripeptide by forming a peptide bond between AA I and AA IV in the presence of a condensing agent to give the peptide of Formula I wherein A is hydrogen;

(I) treating the cyclical quadripeptide formed in Step (H) with

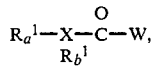

where X, $R_a^2$, and $R_b^2$, are as defined above and W is an acid halide, anhydride, or other carbonyl activating group, to give the peptide of Formula I wherein A is other than hydrogen; and optionally (J) forming a cyclical pentapeptide up to a nonapeptide of AA I, through AA IV or AA IX, by repeating the procedure of Step (E) using protected AA V through protected AA IX, followed by deprotecting of the pentapeptide through nonpeptide to give the peptide of Formula I wherein A is hydrogen, and optionally treating the pentapeptide through nonapeptide as in Step (I) avove to give the peptide of Formula I wherein A is other than hydrogen; the step of cyclizing being carried out as recited in Steps (F), (G), and (H) above, preferably after formation of the complete linear pentapeptide up to nonapeptide, but optionally prior thereto, and also before or after formation of the A substituent; said method also comprising, where necessary, protection of sidechain substituents of the component amino acids AA I through AA IX, with deprotection being carried out as a final step; said method also comprising any combination of the steps set out above, whereby the amino acids I through IX and substituent A is assembled in any desired order to prepare the peptide of Formula I; said method also comprising employment of the steps set out above in a solid phase sequential synthesis, whereby in the initial step the carboxyl group of the selected amino acid is bound to a synthetic resin substrate while the amino group of said amino acid is protected, followed by removal of the protecting group, the succeeding steps being as set out above, the peptide as it is assembled being attached to said synthetic resin substrate; followed by a step of removing the peptide from said synthetic resin substrate by transesterification with methanol to give the methyl ester of AA I, followed by hydrolysis and cyclization as recited above; removal of sidechain protecting groups being accomplished either before or after removal of the peptide from said synthetic resin substrate; the steps of cyclization and formation of the A substituent in said method being accomplished at any time and in any order during preparation of peptides of different linear extent, after preparation of the minimal qudripeptide as recited above.

A preferred method involves preparation of the peptide of desired linear extent and desired A substituent by solid phase sequential synthesis, which is then removed by transesterification to give the linear, protected (N-terminus) methyl ester. The N-terminus protecting group, preferably benzyloxycarbonyl or chlorobenzyloxycarbonyl, is removed by catalytic hydrogenation, followed by hydrolysis of the methyl ester using potassium hydroxide in water and dioxane. Cyclization is then effected using diphenylphosphorylazide in dimethylformamide, using triethylamine, diisopropylethylamine, or sodium bicarbonate as the base additive. Purification is accomplished by silica gel and/or sephadex gel chromatography.

An homologous amino acid is substituted in the solid phase step corresponding to addition of position-8. The preferred position-8 substitution is L-homophenylalanine, which is commercially available in chirally pure form. This N$^\alpha$-BOC-L-2-phenylethylalanine is incorporated during solid phase synthesis as the N-$\alpha$-BOC derivative, as with other amino acids, and requires no special treatment. Preparation of other homologous amino acids for substitution at the 8-position, and as statine derivatives, may be carried out in a straightforward manner using known methods. For example, synthesis of BOC-DL-BisHomoPhe is accomplished in accordance with the procedure schematically represented below:

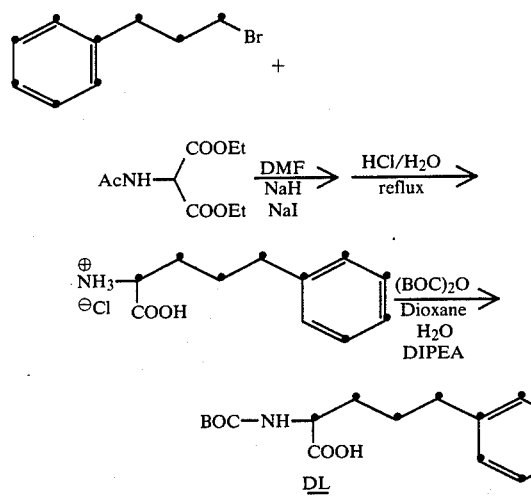

The phenyl analog of statine, (3S,4S)-4-amino-3-hydroxy-5-phenylpentanoic acid (AHPPA) can be prepared in accordance with the procedure described by Rich et al., *J. Med. Chem.* 23: 27–33 (1980).

Other analogs of statine may be prepared in a straightforward manner. For example, the cyclohexylalanine analog of statine, (3S,4S)-4-amino-5-cyclohexyl-3-hydroxypentanoic acid (ACHPA) can be prepared by catalytic hydrogenation (using $H_2$/Rh on alumina, or other suitable catalyst) of the BOC-AHPPA, prepared as described in the paragraph immediately above. Alternatively, this and similar statine analogs can be prepared in accordance with the procedure described for statine, where the BOC-Leu starting material is replaced with the amino acid containing the desired side chain. Thus, BOC-ACHPA can also be prepared starting from BOC-L-cycohexylalanine, itself prepared, for example, by catalytic reduction of BOC-Phe, in the same manner as described for BOC-AHPPA.

The novel inhibitory peptides of the present invention are prepared by using the solid phase sequential synthesis technique.

In the following description several abbreviated designations are used for the amino acid components, certain preferred protecting groups, reagents and solvents. The meanings of such abbreviated designations are given below in Table I.

TABLE I

| Abbreviated Designation | |
|---|---|
| | Amino Acid |
| AHPPA | (3S,4S)—4-amino-3-hydroxy-5-phenylpentanoic acid |
| ACHPA | (3S,4S)—4-amino-5-cyclohexyl-3-hydroxypentanoic acid |
| Ala | L-alanine |
| Arg | L-arginine |
| DAB | 2-S—amino-4-aminobutyric acid |
| Gly | L-glycine |
| His | D or L-histidine |
| HLys | homolysine, 2S—amino-6-aminoheptanoic acid |
| Hph | L-homophenylalanine |

TABLE I-continued

| Abbreviated Designation | |
|---|---|
| Ile | L-isoleucine |
| Leu | L-leucine |
| Lys | L-lysine |
| Met | L-methionine |
| Orn | L-ornithine |
| Phe | L-phenylalanine |
| Ser | L-serine |
| Sar | L-sarcosine (N—methylglycine) |
| Sta | (3S,4S)—statine |
| Thr | L-threonine |
| Trp | L-tryptophan |
| Tyr | L-tyrosine |
| Val | L-valine |
| | Protecting Groups |
| BOC | tert-butyloxycarbonyl |
| CBZ | benzyloxycarbonyl |
| 2-Cl—CBZ | 2-chlorobenzyloxycarbonyl |
| IBU | iso-butyryl |
| IVA | iso-valeryl |
| DNP | dinitrophenyl |
| OMe | methyl ester |
| | Activating Groups |
| HBT | 1-hydroxybenzotriazole |
| | Condensing Agents |
| DCCI | dicyclohexylcarbodiimide |
| DPPA | diphenylphosphorylazide |
| | Reagents |
| TEA | triethylamine |
| TFA | trifluoroacetic acid |
| | Solvents |
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptides of the present invention by the solid phase technique is conducted in a stepwise manner on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONP ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyoxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the -amino group of Lys can be protected by the INOC group or the 2-chlorobenzyloxycarbonyl (2-Cl-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptides of the present invention utilizing the solid phase technique is illustrated in the following examples, which however, are not intended to be any limitation of the present invention.

EXAMPLE 1

N—isobutyryl-L—Histidyl-L—Prolyl-L—Homophenylalanyl-L—Homolysyl-(3S,4S)—Statyl-L—Leucyl-L—Phenylalanyl The title peptide, where the bracket beneath the name indicates the points of cyclization, from the terminal zeta-amino group of the L-Homolysyl residue to the carboxyl group of the L-Phenylalanine residue by an amide link, is prepared by a combination of solid phase and solution methods. The unavailability of L-Homolysine necessitates the synthesis of a suitably protected DL-compound, which is incorporated into the peptide to produce a mixture of two diastereomers as final products, which can be separated and identified as to D- or L- (the L- being preferred) at the final stage. Alternatively, separation of amino acid isomers of DL-homolysine can be accomplished by well-known methods to give the L-isomer, which can be incorporated above into the growing peptide. When the L-isomer is available (as in the case of the analogous L-lysine analog) the incorporation of the single isomer is to be preferred.

L-Homophenylalanine, on the other hand, is readily available, and its use is to be preferred to the use of DL-homophenylalanine, which results in two diastereomers which must be separated.

The synthesis of α-BOC-zeta-CBZ-homolysine (DL), using several modifications of techniques described by other workers (S. Takagi and K. Hayashi, *Chem. Pharm. Bull.* 7, 183 (1959); R. Goudry, *Can. J. Chem.* 31 1060 (1953); A. Paquet, *Can. J. Chem.* 54 733 (1976), is briefly outlined in the accompanying scheme:

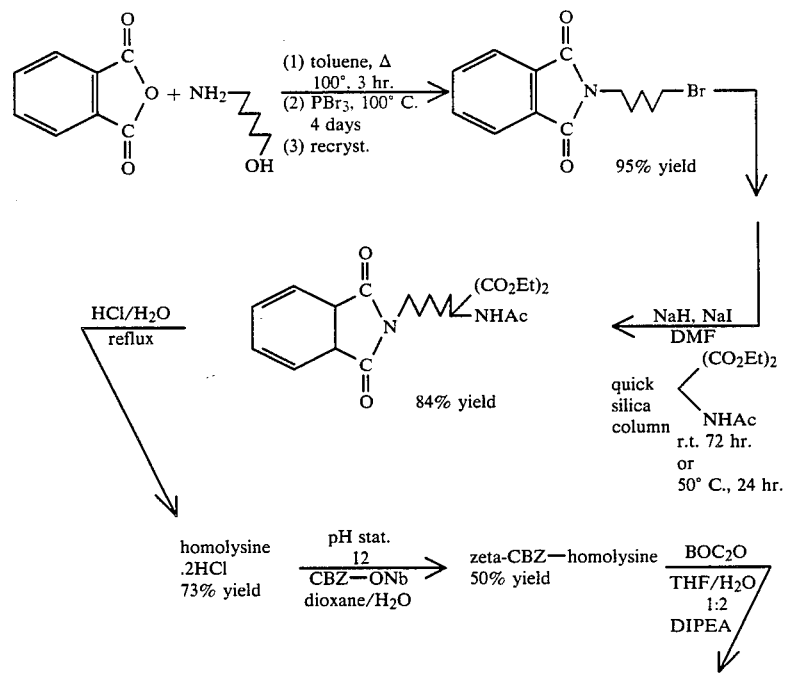

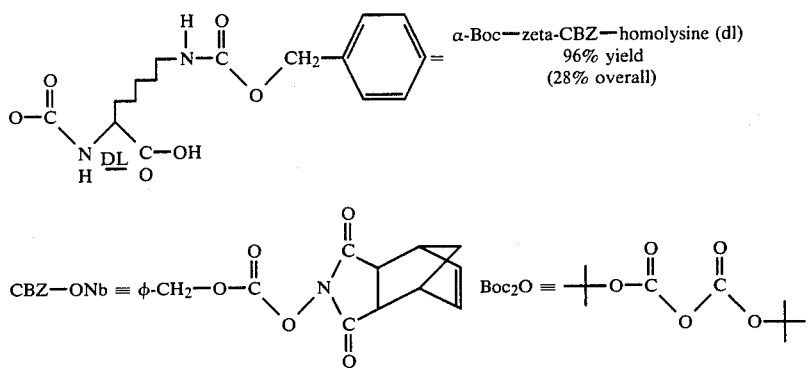

α-Boc—zeta-CBZ—homolysine (dl)
96% yield
(28% overall)

Step A:
N-isobutyryl-L-Histidyl-L-Prolyl-L-Homophenylalanyl-DL-(zeta-CBZ)-Homolysyl-(3S,4S)-Statyl-L-Leucyl-L-Phenylalanyl-O-Resin The title peptide resin is prepared by standard solid phase methodology, as described in Erickson & Merrifield, Proteins, 3rd. ed., 2 257–527, 1971, using a Beckman 990B peptide synthesizer to carry out the operations according to the attached programs. The starting polymer is BOC-Phe esterified to 2% cross-linked polystyrene-divinylbenzene (6 mmol, 5.0 g). The $N^\alpha$-BOC derivatives of His-(DNP), Pro, Phe, and Leu are coupled using dicyclohexylcarbodiimide with an equivalent of the additive 1-hydroxybenzotriazole hydrate. The Sta is prepared in accordance with Rich, et al., J. Org. Chem. 43 3624, 1978. The BOC-group is removed with 40% trifluoroacetic acid. A coupling of 60 minutes followed by a recoupling of 120 minutes (2.5 equivalents each time of BOC-amino acid are used for each amino acid except Sta, L-homophenylalanine, and zeta-CBZ-homolysine). In order to conserve the amounts of the latter two, an initial coupling of 1.25 equivalents of BOC-amino acid (in 1:1 $CH_2Cl_2$/DMF), with DCC and 1 equivalent of $HBT \cdot H_2O$) for 18 hours is followed by steps 1–3 of the recouple program 2 and an additional coupling of 18 hours using the original (saved) coupling solution. This effects greater than 99% complete reaction of the residues, preserving their supply. The N-terminal isobutyryl group is coupled for 30 minutes as a symmetrical anhydride generated in situ from 5.0 equivalents of isobutyric acid and 2.5 equivalents of DCC. This is followed by a recoupling also using the symmetrical anhydride. The DNP-protecting group on His is removed in the final program using two 25-minute treatments with 10% thiophenol in DMF. The finished resin is dried in vacuo.

Step B:
N-isobutyryl-L-Histidyl-L-Prolyl-L-Homophenylalanyl-DL-Homolysyl-(3S,4S)-Statyl-L-Leucyl-L-Phenylalanine A one-quarter portion (nominally 1.5 mmole) of the above (A) resin peptide, approximately 3.5 g, is suspended in 50 ml methanol under nitrogen, to which 5 ml diisopropylethylamine (DIPEA) is added. The suspension is stirred for 3.5 hours, filtered and the residue resuspended as above and stirred for 3 hours, filtered, and resuspended as above for a final 18 hours and filtered. The combined filtrates are evaporated to give crude IBU-His-Pro-L-Homo-Phe-DL-(azeta-CBZ)-Homolys-Sta-Leu-Phe-$OCH_3$. This crude material is dissolved in 10 ml ethyl acetate and washed three times with 30 ml water. The ethyl acetate is dried over $Na_2SO_4$, filtered, and the solution evaporated giving a yellow powder, which is revealed to be predominantly one compound by HPLC and TLC analyses. At this stage the two expected diastereomers, due to use of DL-homolysine, do not separate.

The crude material is hydrogenated in 40 ml ethanol containing 3 ml acetic acid and 3 ml water using 800 mg 10% Pd/C under 50 lbs. pressure of hydrogen in a Parr apparatus, for 3.5 hours. The solution is filtered to remove catalyst and evaporated to give the crude free amine, IBU-His-Pro-L-HomoPhe-DL-Homolys-Sta-Leu-Phe-$OCH_3$, as its diacetic acid hydrated salt.

A portion of this material is dissolved in 40 ml 1:1 dioxane:water into which is added over 3 hours approximately 38 ml 0.1N HCl at a rate necessary to keep the "pH" between 10.5 and 11.5 on a pH meter adjusted to "pH 10" with a 1:1 mixture of pH 10 buffer and dioxane. The hydrolysis reaction can be followed by TLC, 60:40:3:6 chloroform:methanol:water:ammonium hydroxide. The dioxane is stripped from the solution and the pH adjusted to 6.5 with 0.1N HCl. The solution is extracted 2×120 ml with n-butanol and the butanol is evaporated. The residue is triturated with ether and dried to give a white solid, predominantly two spots on TLC and two peaks on HPLC representing the two expected diastereomeric products: IBU-His-Pro-L-HomoPhe-D- or L-Homolys-Sta-Leu-Phe.

Step C:
N-isobutyryl-L-Histidyl-L-Prolyl-L-Homophenylalanyl-L-Homolysyl-(3S,4S)-Statyl-L-Leucyl-L-Phenylalanyl The linear material above (B) is cyclized by dissolving a portion in 50 ml dimethylformamide to which is added approximately 1 equivalent $LiN_3$, approximately 1 equivalent diisopropylethylamine, and approximately 6 equivalents $NaHCO_3$. The solution over $N_2$ is cooled to 0° C., approximately 4 equivalents diphenylphosphorylazide is added, and the solution is stirred at 0° C. for 72 hours. Examination by TLC reveals loss of starting material and two new product spots. The reaction mixture is evaporated and the residue partitioned between 200 ml n-butanol and 50 ml water. The n-butanol layer is washed 3 times with 25 ml 5% $NaHCO_3$, once with 50 ml water and stripped of solvent to give crude cyclic material.

A 0.250 g portion of this crude material is applied to a silica gel column (particle size 0.040 to 0.063 mm, 2.5×55 cm) packed in 100:15:1.5:1.0, chloroform:methanol:water:acetic acid and eluted with the same solvent. The pure faster running spot is isolated and designated Isomer A, and slower running diastereomer is obtained and designated Isomer B. Both can be precipitated from ethyl acetate/ether. The use of 300 MHz 'H NMR unambiguously identifies one isomer A as the desired diastereomer,

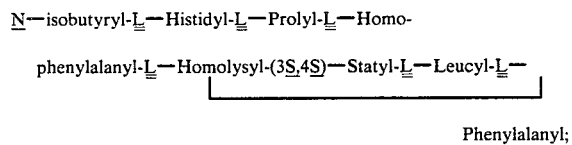

Phenylalanyl; by comparison with similar cyclic compounds containing an L-amino acid, such as L-Lysine, in place of homolysine, the synthesis of which is begun from the pure L-Lysine isomer. The identity of the cyclic product as the monomeric product is confirmed by fast atom bombardment mass spectrometry.

EXAMPLE 2

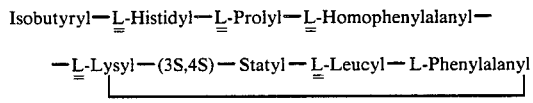

The title peptide is prepared by standard solid phase methodology as described in Erickson and Merrifield, *Proteins*, 3rd ed., 2: 257–527, 1976, using a Beckman Model 990B peptide synthesizer to carry out the operations according to the attached programs. Cyclization of the de-protected linear peptide is effected using diphenylphosphoryl azide in DMF containing an excess of sodium bicarbonate.

Step A:
Isobutyryl-L-Histidyl-L-Prolyl-L-Homophenylalanyl-(N-2-chloro-benzyloxycarbonyl)-L-Lysyl-(3S,4S)-Statyl-L-Leucyl-L-Phenylalanyl-O-Resin The starting polymer resin was BOC-Phe esterified to 2% cross-linking polystyrene-divinylbenzene (2 mmol, 1.65 g). The $N^\alpha$-BOC-derivatives of Leu, Sta, N 2-Cl-CBZ-Lys, L-HomoPhe, Pro, and His-DNP were coupled using dicyclohexylcarbodiimide with an equivalent of the additive 1-hydroxybenzotriazole hydrate. The Sta is prepared according to Rich, et al., *J. Org. Chem.* 43: 3624, 1978. The BOC-group is removed with 40% trifluoroacetic acid. A coupling of 30 minutes followed by a recoupling of 60 minutes (2.5 equivalents each time of BOC-amino acid) are used for each amino acid, except for Sta and L-HomoPhe. These coupling times have been demonstrated previously to give complete coupling (as judged by the method of Kaiser) in this sequence. An additional recoupling of His is performed following Pro. In order to conserve the amounts of Sta and L-HomoPhe employed, an initial coupling using 1.25 equivalents of BOC-Sta and BOC-L-HomoPhe plus equal amounts of HBT and DCCI are stirred in the coupling step in 18 ml 1:1 DMF/CH$_2$Cl$_2$, for 6 hours, followed by a recouple of 6 hours using the same saved coupling solution, without the addition of more DCCI. This is found to give complete coupling. The N-terminal isobutyryl group is coupled for 30 minutes as the symmetrical anhydride formed in situ from 5.0 equivalents of isobutyric acid and 2.5 equivalents of DCCI (no HBT). This is followed by a recoupling similarly. The DNP protecting group on His is removed in the final program using two 25-minute treatments with 10% thiophenol in DMF. The finished resin peptide (3.2 g) is dried and suspended in 40 ml of dry methanol.

Step B:
Isobutyryl-L-Histidyl-L-Prolyl-L-Homophenylalanyl-L-Lysyl-(3S,4S)-Statyl-L-Leucyl-L-Phenylalanine To the suspension prepared in (A) above is added 10 ml diisopropylethylamine, and the reaction mixture is stirred under dry nitrogen for 18 hours. The mixture is then filtered and the resin beads washed with methanol and CH$_2$Cl$_2$. The yellow solution (combined all filtrates) is evaporated under reduced pressure to give crude methyl ester. This crude product is dissolved in 50 ml of methylene chloride containing 5 ml methanol and washed with water. The organic lower layer is dried over sodium sulfate and evaporated to give a yellow powder. This crude material can be purified on silica gel to give IBU-His-Pro-L-HomoPhe-(Cl-CBZ)-Lys-Sta-Leu-Phe-OCH$_3$, but is most conveniently carried on to the next step without purification. Hydrolysis of the methyl ester is effected in 100 ml 1:1 dioxane (peroxide free), water, using 1N NaOH dripped in slowly over 3 hours. Evaporation of the dioxane and extraction of the aqueous layer with CH$_2$Cl$_2$ removes some impurities and yellow color from the aqueous layer, containing the peptide. Neutralization of the aqueous layer with an equivalent of 1N HCl, gives an oily precipitate, which is extracted into ethyl acetate, dried and evaporated to give the free acid. This material is dissolved in 30 ml ethanol containing 2 ml water and 1 ml acetic acid and hydrogenated on a Parr apparatus at 40 lbs. H$_2$ pressure using 0.2 g Pd/C catalyst for 5 hours. After TLC reveals the complete removal of the Cl-CBZ group, the solution is filtered through a Celite pad, and evaporated. The residue is dissolved in water (30 ml) and the pH adjusted to pH 6.5 with 0.1N NaOH, causing some precipitate to form. At this pH, the approximate isoelectric point for the Zwitterion product (the mean of the pKa's of the Lys-amine and Phe-carboxyl), the product can be cleanly extracted into n-butanol, which can be washed with water, and the n-butanol evaporated to give crude IBU-His-Pro-L-HomoPhe-Lys-Sta-Leu-Phe, B.

Step C:
Isobutyryl—L-Histidyl—L-Prolyl—L-Homophenylalanyl—
—L-Lysyl—(3S,4S)—Statyl—L-Leucyl—L-Phenylalanyl A 0.5 g portion (nominally 0.5 mmol) of the crude linear peptide, described in (B) is dissolved in 50 ml dry, degassed DMF in which 0.42 g (10 equivalents) of sodium bicarbonate is suspended. The solution is cooled to 0° C. and stirred. To this solution is added 0.41 g (0.323 mL) diphenylphosphoryl azide (3 equivalents) and the stirring continued for 48 hours. The solution is then evaporated, and the residue suspended in ethyl acetate and washed with water. The ethyl acetate layer is dried and evaporated to give the crude product residue which is dissolved in 50% acetic acid and applied to a Sephadex G-25 column packed in 50% acetic acid. Fractionation, primarily by molecular size, on this column gives a major peptide-containing peak, detected by ultraviolet spectroscopy at 210 nm, which proves to be monomeric material. This peak is collected and evaporated to give a moderately pure material as judged by TLC. Purification by silica gel chromatography (500 g silica; 0.04–0.063 mm particle size; 80:15:0.75:0.75, chloroform:methanol:water:acetic acid) gives a pure product after evaporation and precipitation from $CH_2Cl_2$/ether and drying. $^1H$ NMR (360 MHz): spectrum is consistent with structure. Fast atom bombardment mass spectrometry confirms MW 997 as expected for the cyclic monomeric product.

| Step | Solvent/Reagent | Vol. (ml) | Mix time (min) |
|---|---|---|---|
| | SCHEDULE OF STEPS FOR 6 MMOL RUN | | |
| | Coupling Program 1 | | |
| 1 | $CH_2Cl_2$ | 6 × 60 | 2 |
| 2 | 40% TFA in $CH_2Cl_2$ | 1 × 60 | 2 |
| 3 | 40% TFA in $CH_2Cl_2$ | 1 × 60 | 25 |
| 4 | $CH_2Cl_2$ | 3 × 60 | 2 |
| 5 | 10% TEA in $CH_2Cl_2$ | 2 × 60 | 5 |
| 6 | $CH_2Cl_2$ | 3 × 60 | 2 |
| 7 | BOC—amino acid, HBT in 1:1 DMF/$CH_2Cl_2$ | 40 | 5 |
| 8 | 1.0 M DCCI in $CH_2Cl_2$ | 15 | 60 |
| 9 | DMF | 1 × 60 | 2 |
| 10 | MeOH | 2 × 60 | 2 |
| 11 | $CH_2Cl_2$ | 1 × 60 | 2 |
| | Re-Couple Program 2 | | |
| 1 | $CH_2Cl_2$ | 1 × 60 | 2 |
| 2 | 10% TEA in $CH_2Cl_2$ | 2 × 60 | 5 |
| 3 | $CH_2Cl_2$ | 3 × 60 | 2 |
| 4 | BOC—amino acid, HBT in 1:1 DMF/$CH_2Cl_2$ | 40 | 5 |
| 5 | 1.0 M DCCI in $CH_2Cl_2$ | 15 | 120 |
| 6 | DMF | 1 × 60 | 2 |
| 7 | MeOH | 2 × 60 | 2 |
| 8 | $CH_2Cl_2$ | 5 × 60 | 2 |
| | Program 3 (DNP removal) | | |
| 1 | $CH_2Cl_2$ | 1 × 60 | 2 |
| 2 | DMF | 2 × 60 | 2 |
| 3 | 10% phenylthiol in DMF | 1 × 60 | 25 |
| 4 | DMF | 1 × 60 | 2 |
| 5 | 10% TEA in $CH_2Cl_2$ | 1 × 60 | 2 |
| 6 | DMF | 2 × 60 | 2 |
| 7 | 10% phenylthiol in DMF | 1 × 60 | 25 |
| 8 | DMF | 3 × 60 | 2 |
| 9 | MeOH | 2 × 60 | 2 |
| 10 | $CH_2Cl_2$ | 2 × 60 | 2 |
| 11 | MeOH | 2 × 60 | 2 |
| 12 | $CH_2Cl_2$ | 2 × 60 | 2 |
| 13 | MeOH | 2 × 60 | 2 |

EXAMPLE 3–13

Following the standard solid phase methodology described above in Example 1, additional inhibitory peptides of the present invention are prepared. The peptides prepared are set out in the following table. Satisfactory amino acid analyses are obtained by Spinco method for each listed peptide.

| Exm. No. | Peptide |
|---|---|
| | IBU—His—Pro—Hph—Orn—Sta—Leu—Phe⎤ |
| | IBU—His—Pro—Hph—DAB—Sta—Leu—Phe—Gly⎤ |
| | IBU—His—Pro—Hph—Orn—Sta—Leu—Phe—Gly⎤ |
| | IBU—His—Pro—Hph—Lys—Sta—Leu—Phe—Gly⎤ |
| | BOC—Hph—Lys—Sta—Leu—Phe⎤ |
| | IVA—His—Pro—Hph—Lys—Sta—Leu—Phe⎤ |
| | IVA—His—Pro—Hph—Lys—AHPPA—Leu—Phe⎤ |
| | BOC—Hph—Lys—ACHPA—Ile—His⎤ |
| | IVA—His—D-Pro—Hph—Lys—AHPPA—Leu—Phe⎤ |
| | IVA—His—D-Pro—Hph—Lys—ACHPA—Leu—Phe⎤ |
| | IVA—His—D-Pro—Hph—Lys—ACHPA—Ile—His⎤ |

For the peptides prepared above, various analytical methods are carried out to verify the structure of the peptide products.

What is claimed is:

1. A peptide of the formula:

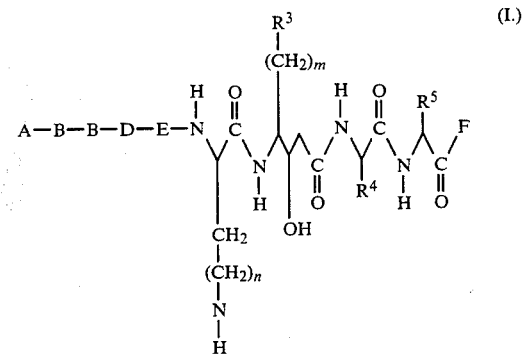

(I.)

wherein:

A is hydrogen; or

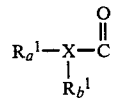

where
X is —O—; —O—CH—; —CH—O—; —CH—; —NH—CH—; or —S—CH—; and
$R_a^1$ and $R_b^1$ are independently hydrogen; Y—$(CH_2)_p$— or Y—$(CH_2)_{p'}$—CH= CH—$(CH_2)_{p''}$, where Y is $C_{1-4}$alkyl, hydrogen, or unsubstituted or mono- or disubstituted $C_{3-7}$-cycloalkyl, phenyl or naphthyl, wherein the one or two substituents are independently selected from the group consisting of $C_{1-8}$alkyl, trifluoromethyl, hydroxy, $C_{1-4}$alkoxy, and halo;

p is 0 to 5; and p' and p" are independently 0, 1 or 2; except that where X is —O—, only one of $R_a^1$ and $R_b^1$ is present;

B is absent; glycyl, sarcosyl; or

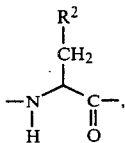

where $R^2$ is hydrogen; $C_{1-4}$alkyl; hydroxy $C_{1-4}$alkyl; indolyl; 4-imidazolyl; amino $C_{2-4}$alkyl; guanidyl, $C_{2-3}$alkyl; methylthiomethyl; or unsubstituted or mono- or disubstituted phenyl or naphthyl, wherein the one or two substituents are independently selected from $C_1$-$C_4$-alkyl, trifluoromethyl, hydroxy, $C_1$-$C_4$-alkoxy and halo;

D is absent;

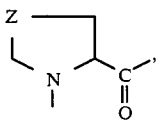

where Z is —(CH$_2$)$_l$— and l is 1 or 2; or —S—;

E is

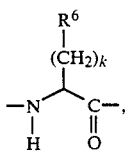

where k is 2 to 4; and $R^6$ is hydrogen; $C_{1-4}$alkyl; indolyl; or unsubstituted or mono- or disubstituted phenyl or naphthyl, where the one or two substituents are independently selected from the group consisting of $C_{1-4}$alkyl, trifluoromethyl, hydroxy, $C_{1-4}$alkoxy, and halo;

F is absent or glycyl;

$R^3$ is $C_{3-6}$alkyl; or unsubstituted or mono- or disubstituted $C_{3-7}$cycloalkyl, phenyl or naphthyl, where the one or two substituents are independently selected from the group consisting of $C_{1-4}$alkyl, trifluoromethyl, hydroxy, $C_{1-4}$alkoxy, and halo;

$R^4$ is hydrogen; or

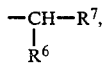

where $R^7$ is hydrogen; $C_{1-4}$alkyl; hydroxy; or $C_{3-7}$cycloalkyl; and $R^6$ is as defined above;

$R^5$ is hydrogen;

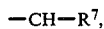

where $R^6$ and $R^7$ are as defined above; or —(CH$_2$)$_q$—$R^8$, where q is 0 or 1-4; and $R^8$ is an unsubstituted or mono- or disubstituted heterocycle, representing a 5- or 6-membered ring or benzofused 5- or 6-membered ring comprising one or two heteroatoms independently selected fron N, O and S, where the one or two substituents are independently selected from the group consisting of $C_{1-6}$alkyl, hydroxy, trifluoromethyl, $C_{1-4}$alkoxy, halo, phenyl, naphthyl, phenyl-$C_1$-$C_4$-alkyl, naphthyl-$C_1$-$C_4$-alkyl, amino, and mono- or di-$C_{1-4}$alkylamino; guanidyl $C_{2-3}$alkyl; or amino $C_{1-4}$alkyl;

m is 1 to 4;

n is 0 to 4; and wherein all of the asymmetric carbon atoms have an S configuration, except for those in the A, B and D substituents, which may have an S or R configuration; and a pharmaceutically acceptable salt thereof.

2. A peptide according to claim 1 wherein the peptide is a member selected from the group consisting essentially of:

IBU—His—Pro—Hph—Lys—Sta—Leu—Phe ⌐
         └_____⌉

IBU—His—Pro—Hph—Orn—Sta—Leu—Phe ⌐
         └_____⌉

IBU—His—Pro—Hph—DAB—Sta—Leu—Phe—Gly ⌐
         └_____⌉

IBU—His—Pro—Hph—HLys—Sta—Leu—Phe ⌐
         └_____⌉

IBU—His—Pro—Hph—Orn—Sta—Leu—Phe—Gly ⌐
         └_____⌉

IBU—His—Pro—Hph—Lys—Sta—Leu—Phe—Gly ⌐
         └_____⌉

BOC—Hph—Lys—Sta—Leu—Phe ⌐
         └_____⌉

IVA—His—Pro—Hph—Lys—Sta—Leu—Phe ⌐
         └_____⌉

IVA—His—Pro—Hph—Lys—AHPPA—Leu—Phe ⌐
         └_____⌉

BOC—Hph—Lys—ACHPA—Ile—His ⌐
         └_____⌉

IVA—His—D-Pro—Hph—Lys—AHPPA—Leu—Phe ⌐
         └_____⌉

IVA—His—D-Pro—Hph—Lys—ACHPA—Leu—Phe ⌐
         └_____⌉

IVA—His—D-Pro—Hph—Lys—ACHPA—Ile—His ⌐
         └_____⌉

3. A pharmaceutical composition for treating renin-associated hypertension or renin-associated a hyperaldosteronism, comprising a pharmaceutical carrier and a therapeutically effective amount of the a peptide of the formula:

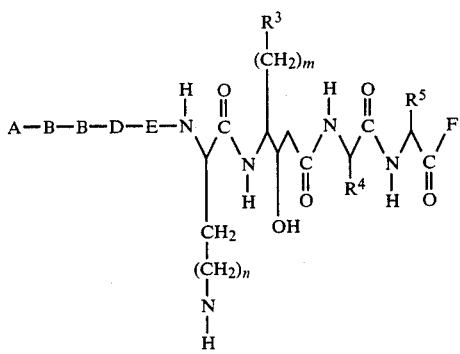 (I.)

wherein:

A is hydrogen; or

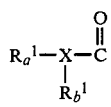

where
X is —O—; —O—CH—; —CH—O—; —CH—;
—NH—CH—; or —S—CH—; and
$R_a^1$ and $R_b^1$ are independently hydrogen; Y—$(CH_2)_p$— or Y—$(CH_2)_{p'}$—CH=CH—$(CH_2)_{p''}$, where Y is $C_{1-4}$alkyl, hydrogen, or unsubstituted or mono- or disubstituted $C_{3-7}$cycloalkyl, phenyl or naphthyl, wherein the one or two substituents are independently selected from the group consisting of $C_{1-8}$alkyl, trifluoromethyl, hydroxy, $C_{1-4}$alkoxy, and halo; p is 0 to 5; and p' and p" are independently 0, 1 or 2; except that where X is —O—, only one of $R_a^1$ and $R_b^1$ is present;

B is absent; glycyl; sarcosyl; or

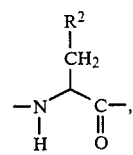

where $R^2$ is hydrogen; $C_{1-4}$alkyl; hydroxy $C_{1-4}$alkyl; indolyl; 4-imidazolyl; amino $C_{2-4}$alkyl; guanidyl $C_{2-3}$ alkyl; methylthiomethyl; or unsubstituted or mono- or disubstituted phenyl or naphthyl, wherein the one or two substituents are independently selected from $C_1$-$C_4$-alkyl, trifluoromethyl, hydroxy, $C_1$-$C_4$-alkoxy and halo;

D is absent;

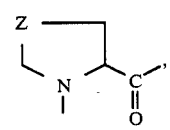

where X is —$(CH_2)_l$— and l is 1 or 2; or —S—;

E is

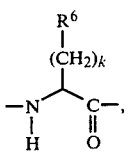

where k is 2 to 4; and $R^6$ is hydrogen; $C_{1-4}$alkyl; indolyl; or unsubstituted or mono- or disubstituted phenyl or naphthyl, where the one or two substituents are independently selected from the group consisting of $C_{1-4}$alkyl, trifluoromethyl, hydroxy, $C_{1-4}$alkoxy, and halo; or F is absent or glycyl;

$R^3$ is $C_{3-6}$alkyl; or unsubstituted or mono- or disubstituted $C_{3-7}$cycloalkyl, phenyl or naphthyl, where the one or two substituents are independently selected from the group consisting of $C_{1-4}$alkyl, trifluoromethyl, hydroxy, $C_{1-4}$alkoxy, and halo;

$R^4$ is hydrogen; or

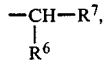

where $R^7$ is hydrogen; $C_{1-4}$alkyl; hydroxy; or $C_{3-7}$cycloalkyl; and $R^6$ is as defined above;

$R^5$ is hydrogen;

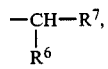

where $R^6$ and $R^7$ are as defined above; or —$(CH_2)_q$—$R^8$, where q is 0 or 1-4; and $R^8$ is an unsubstituted or mono- or disubstituted heterocycle, representing a 5- or 6-membered ring or benzofused 5- or 6-membered ring comprising one or two heteroatoms independently selected from N, O and S, where the one or two substituents are independently selected from the group consisting of $C_{1-6}$alkyl, hydroxy, trifluoromethyl, $C_{1-4}$alkoxy, halo, phenyl, naphthyl, phenyl-$C_1$-$C_4$-alkyl, naphthyl-$C_1$-$C_4$-alkyl, amino, and mono- or di-$C_{1-4}$alkylamino; guanidyl $C_{2-3}$alkyl; or amino $C_{1-4}$alkyl;

m is 1 to 4;

n is 0 to 4; and wherein all of the asymmetric carbon atoms have an S configuration, except for those in the A, B and D substituents, which may have an S or R configuration; and a pharmaceutically acceptable salt thereof.

4. A composition according to claim 3 wherein the peptide is a member selected from the group consisting essentially of:

IBU—His—Pro—Hph—Lys—Sta—Leu—Phe

IBU—His—Pro—Hph—Orn—Sta—Leu—Phe

IBU—His—Pro—Hph—DAB—Sta—Leu—Phe—Gly

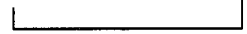
* * * * *

UNITED STATES PATENT AND TRADEMARK OFFICE
CERTIFICATE OF CORRECTION

PATENT NO. : 4,665,052

DATED : May 12, 1987

INVENTOR(S) : J.S. Boger

Page 1 of 5

It is certified that error appears in the above—identified patent and that said Letters Patent is hereby corrected as shown below:

In The Specification:

Col. 3, lines 44-58, please remove

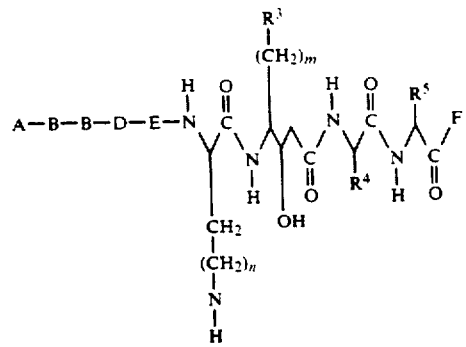

and replace it with

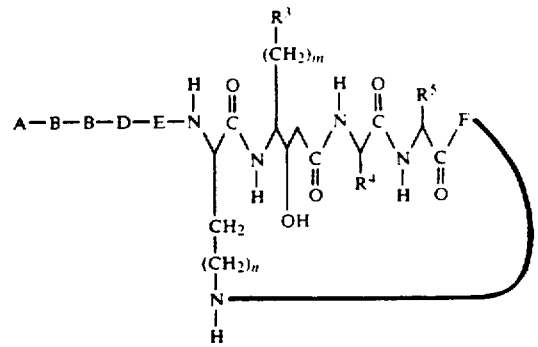

Col. 7, lines 50-60, please remove

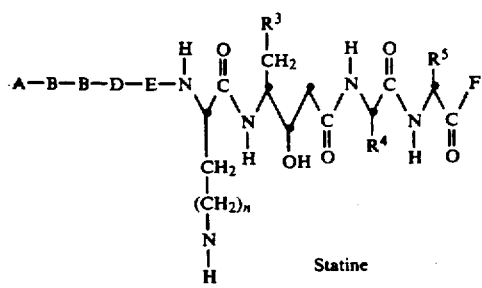

and replace it with

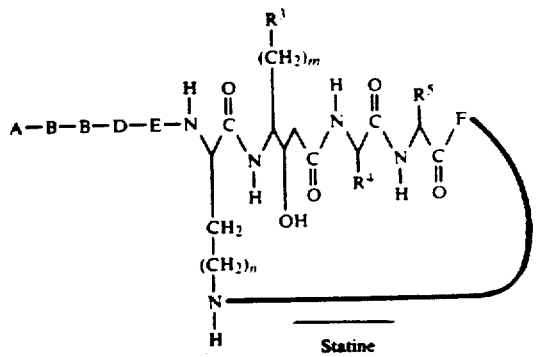

UNITED STATES PATENT AND TRADEMARK OFFICE
CERTIFICATE OF CORRECTION

PATENT NO. : 4,665,052

DATED : May 12, 1987

INVENTOR(S) : J.S. Boger

It is certified that error appears in the above—identified patent and that said Letters Patent is hereby corrected as shown below:

Col. 8, lines 15-25, please remove

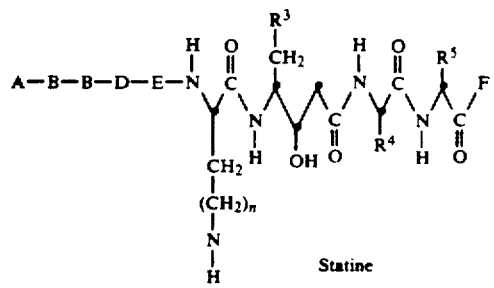

and replace it with

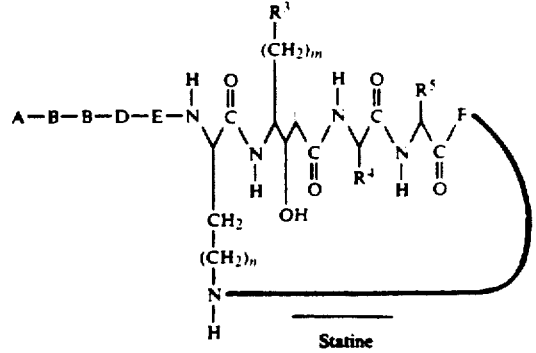

Col. 10, lines 3-13, please remove

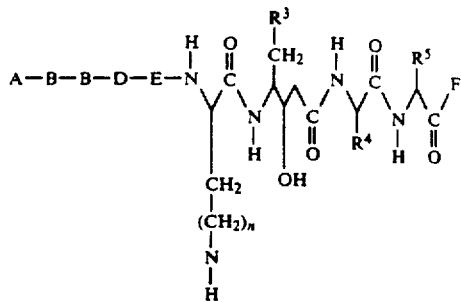

and replace it with

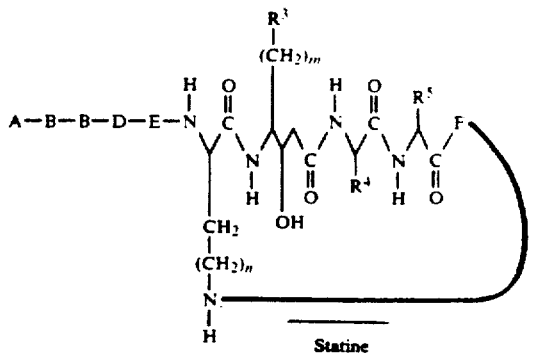

UNITED STATES PATENT AND TRADEMARK OFFICE
CERTIFICATE OF CORRECTION

PATENT NO. : 4,665,052
DATED : May 12, 1987
INVENTOR(S) : J.S. Boger

It is certified that error appears in the above—identified patent and that said Letters Patent is hereby corrected as shown below:

Col. 10, lines 28-40, please remove

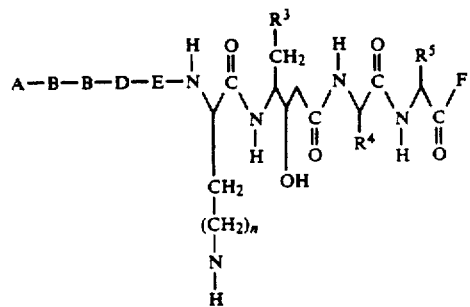

and replace it with

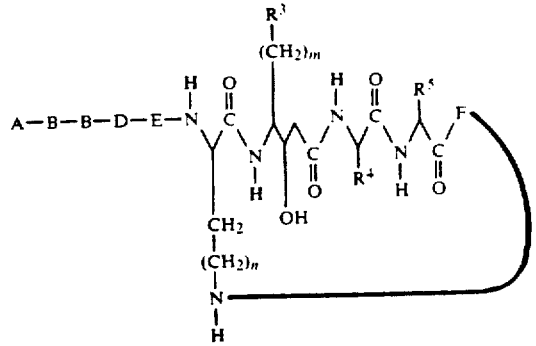

Col. 19, lines 12-15, please remove

N—isobutyryl-L—Histidyl-L—Prolyl-L—Homo-phenylalanyl-L—Homolysyl-(3S,4S)—Statyl-L—Leucyl-L—
Phenylalanyl;

and replace it with

N—isobutyryl-L—Histidyl-L—Prolyl-L—Homo-phenylalanyl-L—Homolysyl-(3S,4S)—Statyl-L—Leucyl-L— Phenylalanyl;

UNITED STATES PATENT AND TRADEMARK OFFICE
CERTIFICATE OF CORRECTION

Page 4 of 5

PATENT NO. : 4,665,052
DATED : May 12, 1987
INVENTOR(S) : J.S. BOGER

It is certified that error appears in the above—identified patent and that said Letters Patent is hereby corrected as shown below:

Col. 22, lines 38-52, please remove

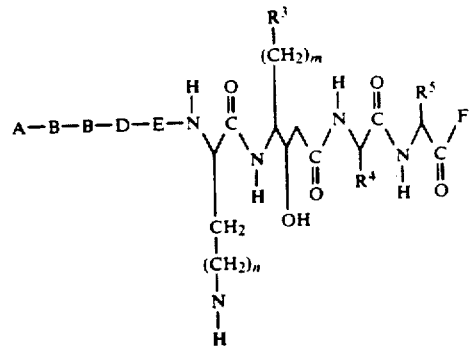

and replace it with

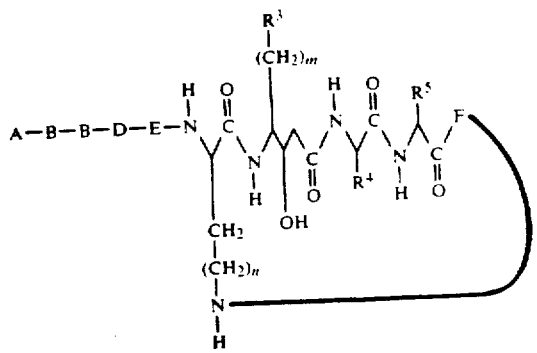

Col. 25, lines 2-15, please remove

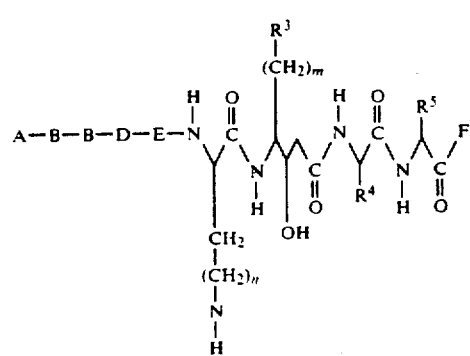

and replace it with

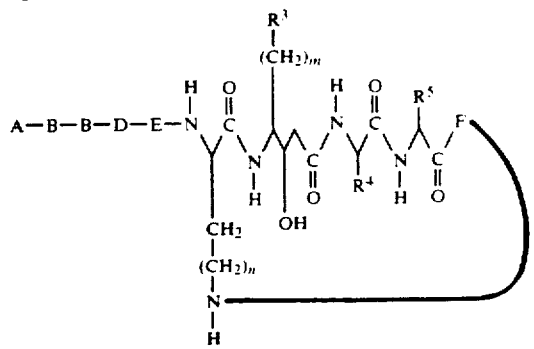

UNITED STATES PATENT AND TRADEMARK OFFICE
CERTIFICATE OF CORRECTION

PATENT NO. : 4,665,052

DATED : May 12, 1987

INVENTOR(S) : J. S. BOGER

It is certified that error appears in the above-identified patent and that said Letters Patent is hereby corrected as shown below:

Column 25, line 67, after "where" and before "is-$(CH_2)_1$-and" please remove "X", and replace it with -- Z --.

Signed and Sealed this

Fifteenth Day of March, 1988

*Attest:*

DONALD J. QUIGG

*Attesting Officer*  *Commissioner of Patents and Trademarks*